US012807163B2

(12) United States Patent
Jeon et al.

(10) Patent No.: US 12,807,163 B2
(45) Date of Patent: Nov. 24, 2026

(54) APPARATUS FOR CONTROLLING A VEHICLE AND METHOD THEREOF

(71) Applicants: Hyundai Motor Company, Seoul (KR); Kia Corporation, Seoul (KR)

(72) Inventors: Seul Ki Jeon, Hwaseong (KR); Hui Won Shin, Hwaseong (KR); Eung Hwan Kim, Hwaseong (KR)

(73) Assignees: Hyundai Motor Company, Seoul (KR); Kia Corporation, Seoul (KR)

( * ) Notice: Subject to any disclaimer, the term of this patent is extended or adjusted under 35 U.S.C. 154(b) by 150 days.

(21) Appl. No.: 18/889,073

(22) Filed: Sep. 18, 2024

(65) Prior Publication Data

US 2025/0214592 A1 Jul. 3, 2025

(30) Foreign Application Priority Data

Jan. 2, 2024 (KR) ........................ 10-2024-0000340

(51) Int. Cl.

| | |
|---|---|
| ***B60W 40/08*** | (2012.01) |
| ***B60W 10/04*** | (2006.01) |
| ***G01N 33/497*** | (2006.01) |
| ***H04W 4/029*** | (2018.01) |

(52) U.S. Cl.

CPC ............ *B60W 40/08* (2013.01); *B60W 10/04* (2013.01); *G01N 33/4972* (2013.01); *H04W 4/029* (2018.02); *B60W 2040/0836* (2013.01); *B60W 2540/043* (2020.02); *B60W 2540/30* (2013.01)

(58) Field of Classification Search

CPC ................. B60W 40/08; B60W 10/04; B60W 2040/0836; B60W 2540/043; B60W 2540/30; B60W 2540/24; B60W 2556/50; B60W 50/14; B60W 2040/0809; B60W 2050/143; B60W 2420/403; G01N 33/4972; H04W 4/029

See application file for complete search history.

(56) References Cited

U.S. PATENT DOCUMENTS

| | | | | |
|---|---|---|---|---|
| 2012/0245763 A1* | 9/2012 | Mizuno ................ | B60K 28/063 701/1 |
| 2024/0083446 A1* | 3/2024 | Yokoyama ............ | B60W 40/09 |

FOREIGN PATENT DOCUMENTS

| | | | |
|---|---|---|---|
| WO | WO-2021219012 A1 * 11/2021 | ........... | B60K 28/063 |

* cited by examiner

*Primary Examiner* — Quan Zhen Wang
*Assistant Examiner* — Mancil Littlejohn, Jr.
(74) *Attorney, Agent, or Firm* — Fox Rothschild LLP

(57) ABSTRACT

A vehicle control device includes a memory, a communication circuit, an alcohol sensor, and a processor. The processor may acquire driver information, acquire a region in which the host vehicle is located, and legal limits for enforcing drunk driving, measure the blood alcohol concentration (BAC) of the driver via the alcohol sensor, and control the host vehicle to come to a stop if the BAC falls within the BAC range in which the driver is subject to sanctions according to the legal limits, the BAC range being determined based on the driver information and the legal limits.

19 Claims, 6 Drawing Sheets

APPARATUS FOR CONTROLLING A VEHICLE AND METHOD THEREOF

CROSS-REFERENCE TO RELATED APPLICATION

This application claims under 35 U.S.C. § 119(a) the benefit of Korean Patent Application No. 10-2024-0000340, filed in the Korean Intellectual Property Office on Jan. 2, 2024, the entire contents of which are incorporated herein by reference.

BACKGROUND

Technical Field

The present disclosure relates to a vehicle control device and method, and more specifically, to a technology for identifying whether a driver's blood alcohol concentration falls within a blood alcohol concentration (BAC) range in which a driver is subject to sanctions according to legal limits for enforcing drunk driving, which are different depending on regions.

Background

With the development of transportation, the incidence of accidents caused by drunk driving has also increased. Previously, to reduce such accidents, authorities measured and cracked down on drivers with high blood alcohol concentrations. However, with recent technological developments have led to the interlock technology. The technology is designed to prevent drunk driving by controlling the vehicle at the pre-driving phase, ensuring that drivers meet legal sobriety standards before they can operate the vehicle.

Alcohol interlock technology activates the vehicle based on a blood alcohol concentration being below legal limits and prevents driving of the vehicle if the driver's blood alcohol concentration exceeds the legal limits. Should the driver's blood alcohol concentration be too high, the vehicle may be disabled, the vehicle's speed is reduced, or a warning notification to a driver is provided.

SUMMARY

The present disclosure has been made to solve the above-mentioned problems occurring in the prior art while advantages achieved by the prior art are maintained intact.

An exemplary embodiment of the present disclosure provides a vehicle control device and method for acquiring drunk driving information that changes depending on a region where a host vehicle is located.

An exemplary embodiment of the present disclosure provides a vehicle control device and method for identifying legal limits for enforcing drunk driving, which vary depending on a driver.

An exemplary embodiment of the present disclosure provides a vehicle control device and method for reducing the incidence of accidents caused by drunk driving.

An exemplary embodiment of the present disclosure provides a vehicle control device and method for improving the accuracy of determination of whether there is drunk driving.

The technical problems to be solved by the present disclosure are not limited to the aforementioned problems, and any other technical problems not mentioned herein will be clearly understood from the following description by those skilled in the art to which the present disclosure pertains.

In one aspect, 1. A vehicle control device is provided comprising: 1) a memory configured to store program instructions; 2) an alcohol sensor configured to measure a blood alcohol concentration (BAC) of a driver operating a host vehicle; and 3) a processor configured to execute the program instructions, wherein the processor is configured to: i) acquire driver information, comprising at least one of an age of the driver, license acquisition date, whether the driver is registered as a commercial driver and information about the driver's driving proficiency; ii) acquire a region in which the host vehicle is located, and legal limits for enforcing drunk driving corresponding to the region; iii) measure the BAC of the driver via the alcohol sensor; iv) identify whether the measured BAC falls within a BAC range in which the driver is subject to sanctions according to the legal limits, the BAC range being determined based on the driver information and the legal limits; and v) control the host vehicle to come to a stop if the BAC falls within the BAC range.

According to an exemplary embodiment of the present disclosure, a vehicle control device includes a memory that stores program instructions, an alcohol sensor that measures a blood alcohol concentration of a driver operating a host vehicle, and a processor that executes the program instructions.

According to an exemplary embodiment, the processor may acquire driver information, including at least one of an age of the driver, license acquisition date, whether the driver is registered as a commercial driver, or information about the driver's driving proficiency, or any combination thereof, acquire a region in which the host vehicle is located, and legal limits for enforcing drunk driving corresponding to the region in which the host vehicle is located, measure the blood alcohol concentration of the driver via the alcohol sensor, identify whether the measured blood alcohol concentration falls within a blood alcohol concentration (BAC) range in which the driver is subject to sanctions according to the legal limits, the BAC range being identified based on the driver information and the legal limits, and control the host vehicle to come to a stop if the blood alcohol concentration falls within the BAC range in which the driver is subject to sanctions according to the legal limits.

According to an exemplary embodiment, the processor may measure the blood alcohol concentration of the driver via the alcohol sensor upon determining at least one of closure of a door of a driver seat where the driver is located in the host vehicle, or fastening of a seat belt of the driver seat, or any combination thereof.

According to an exemplary embodiment, the processor may reacquire the driver information based on occurrence of a driver change event including at least one of opening of the door of the driver seat, unbuckling of the seat belt of the driver seat, or stopping driving after driving, or any combination thereof, and re-measure the blood alcohol concentration of the driver via the alcohol sensor.

According to an embodiment, the processor may acquire at least one BAC limit included in legal limits for enforcing drunk driving corresponding to a specific area including the region in which the host vehicle is located and re-measure the blood alcohol concentration of the driver via the alcohol sensor based on a change in at least one of the at least one BAC limit for enforcing drunk driving, or the region in which the host vehicle is located, or any combination thereof.

According to an exemplary embodiment, the processor may re-measure the blood alcohol concentration of the driver via the alcohol sensor based on, after or before the region in which the host vehicle is located has been changed, a BAC limit included in legal limits for enforcing drunk driving, which corresponds to the region after the change in region being smaller than a BAC limit included in legal limits for enforcing drunk driving, which corresponds to the region before the change in region.

According to an exemplary embodiment, the vehicle control device may further include a camera. The processor may measure the blood alcohol concentration of the driver via the alcohol sensor upon determining that the driver information corresponds to the driver in an authentication method that includes at least one of authentication via the camera, authentication via fingerprint recognition, or authentication via mobile, or any combination thereof.

According to an exemplary embodiment, the processor may control the host vehicle according to the operation of the driver without acquiring the driver information based on occurrence of the driver change event if global positioning system (GPS) information indicating a location of the host vehicle is not received at a boundary of regions with different BAC limits of legal limits for enforcing drunk driving, and reacquire the driver information based on the driver change event identified while the GPS information is not received if the GPS information indicating the location of the host vehicle is received.

According to an exemplary embodiment, the processor may acquire the driver information based on the driver's input for providing the driver information if the host vehicle includes a public vehicle which multiple drivers are able to use, or a commercial vehicle that generates profit through driving, or acquire the driver information via the memory or acquire the driver information via the communication circuit if the host vehicle includes a vehicle other than the public vehicle and the commercial vehicle.

According to an exemplary embodiment, the processor may provide the driver with a notification for guiding the driver to measure the blood alcohol concentration based on a time at which the blood alcohol concentration needs to be measured, or a time at which a BAC limit included in the legal limits changes.

According to an exemplary embodiment, the processor may provide the driver with a route in which the BAC limit included in legal limits for enforcing drunk driving corresponding to each of at least one region included in a route to a destination is kept not smaller than the BAC limit included in legal limits for enforcing drunk driving corresponding to an origin of the route, based on an input for acquiring the route from the driver.

According to an exemplary embodiment, the processor may measure the blood alcohol concentration via the alcohol sensor in response to the driver's operation for measuring the blood alcohol concentration, or measure the blood alcohol concentration via the alcohol sensor regardless of the driver's operation.

According to an exemplary embodiment, the processor may measure the blood alcohol concentration of the driver via the alcohol sensor before turning on an ignition of the host vehicle, and provide the driver with a warning about drunk driving, or re-measure the blood alcohol concentration of the driver via the alcohol sensor after turning on the ignition.

According to an embodiment of the present disclosure, a vehicle control method includes acquiring driver information, including at least one of an age of a driver, license acquisition date, whether the driver is registered as a commercial driver, or information about the driver's proficiency in driving, or any combination thereof, acquiring a region in which a host vehicle is located, and legal limits for enforcing drunk driving corresponding to the region in which the host vehicle is located, measuring the blood alcohol concentration of the driver via an alcohol sensor, identifying whether the measured blood alcohol concentration falls within a BAC range in which the driver is subject to sanctions according to the legal limits, the BAC range being identified based on the driver information and the legal limits, and controlling the host vehicle to come to a stop if the blood alcohol concentration falls within the BAC range in which the driver is subject to sanctions according to the legal limits.

According to an exemplary embodiment, the measuring of the blood alcohol concentration of the driver via the alcohol sensor may include measuring the blood alcohol concentration of the driver via the alcohol sensor upon determining at least one of closure of a door of a driver seat where the driver is located in the host vehicle, or fastening of a seat belt of the driver seat, or any combination thereof.

According to an exemplary embodiment, the vehicle control method may further include reacquiring the driver information based on occurrence of a driver change event including at least one of opening of the door of the driver seat, unbuckling of the seat belt of the driver seat, or stopping driving after driving, or any combination thereof, and re-measuring the blood alcohol concentration of the driver via the alcohol sensor.

According to an exemplary embodiment, the vehicle control method may further include acquiring at least one BAC limit included in legal limits for enforcing drunk driving corresponding to a specific area including the region in which the host vehicle is located, and re-measuring the blood alcohol concentration of the driver via the alcohol sensor based on a change in at least one of the at least one BAC limit for enforcing drunk driving, or the region in which the host vehicle is located, or any combination thereof.

According to an exemplary embodiment, the vehicle control method may further include re-measuring the blood alcohol concentration of the driver via the alcohol sensor based on, after or before the region in which the host vehicle is located has been changed, a BAC limit included in legal limits for enforcing drunk driving, which corresponds to the region after the change in region being smaller than a BAC limit included in legal limits for enforcing drunk driving, which corresponds to the region before the change in region.

According to an exemplary embodiment, the measuring of the blood alcohol concentration of the driver via the alcohol sensor may include measuring the blood alcohol concentration of the driver via the alcohol sensor upon determining that the driver information corresponds to the driver in an authentication method that includes at least one of authentication via the camera, authentication via fingerprint recognition, or authentication via mobile, or any combination thereof.

According to an exemplary embodiment, the vehicle control method may further include controlling the host vehicle according to the operation of the driver without acquiring the driver information based on occurrence of the driver change event if global positioning system (GPS) information indicating a location of the host vehicle is not received at a boundary of regions with different BAC limits of legal limits for enforcing drunk driving, and reacquiring the driver information based on the driver change event identified while the GPS information is not received if the GPS information indicating the location of the host vehicle is received.

According to an exemplary embodiment, the acquiring of the driver information, including at least one of the age of the driver, the license acquisition date, whether the driver is registered as the commercial driver, or information about the driver's proficiency in driving, or any combination thereof may include acquiring the driver information based on the driver's input for providing the driver information if the host vehicle includes a public vehicle which multiple drivers are able to use, or a commercial vehicle that generates profit through driving, or acquiring the driver information via a memory or acquiring the driver information via a communication circuit if the host vehicle includes a vehicle other than the public vehicle and the commercial vehicle.

BRIEF DESCRIPTION OF THE DRAWINGS

The above and other objects, features and advantages of the present disclosure will be more apparent from the following detailed description taken in conjunction with the accompanying drawings.

DETAILED DESCRIPTION

Figure 1:
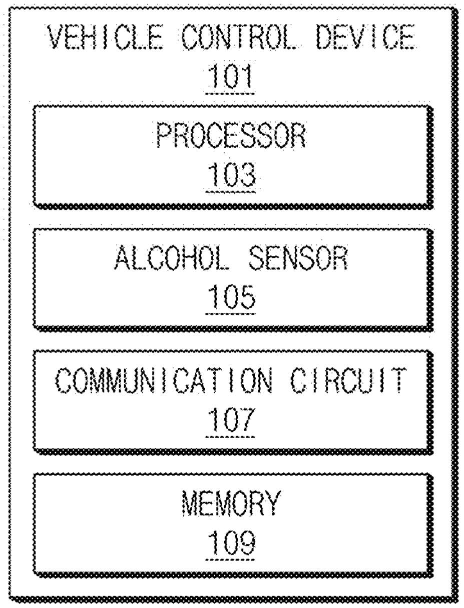
FIG. 1 is a block diagram showing the configuration of a vehicle control device according to an exemplary embodiment of the present disclosure.

Hereinafter, some embodiments of the present disclosure will be described in detail with reference to the exemplary drawings. In adding the reference numerals to the components of each drawing, it should be noted that the identical or equivalent component is designated by the identical numeral even when they are displayed on other drawings. Further, in describing the embodiment of the present disclosure, a detailed description of well-known features or functions will be ruled out in order not to unnecessarily obscure the gist of the present disclosure.

In describing the components of the embodiment according to the present disclosure, terms such as first, second, "A", "B", (a), (b), and the like may be used. These terms are merely intended to distinguish one component from another component, and the terms do not limit the nature, sequence or order of the constituent components. Unless otherwise defined, all terms used herein, including technical or scientific terms, have the same meanings as those generally understood by those skilled in the art to which the present disclosure pertains. Such terms as those defined in a generally used dictionary are to be interpreted as having meanings equal to the contextual meanings in the relevant field of art, and are not to be interpreted as having ideal or excessively formal meanings unless clearly defined as having such in the present application.

In addition, in the present disclosure, the expressions "greater than" or "less than" may be used to indicate whether a specific condition is satisfied or fulfilled, but are used only to indicate examples, and do not exclude "greater than or equal to" or "less than or equal to". A condition indicating "greater than or equal to" may be replaced with "greater than", a condition indicating "less than or equal to" may be replaced with "less than", a condition indicating "greater than or equal to and less than" may be replaced with "greater than and less than or equal to". In addition, 'A' to 'B' means at least one of elements from A (including A) to B (including B).

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The terminology used herein is for the purpose of describing particular embodiments only and is not intended to be limiting of the disclosure. As used herein, the singular forms "a," "an" and "the" are intended to include the plural forms as well, unless the context clearly indicates otherwise. These terms are merely intended to distinguish one component from another component, and the terms do not limit the nature, sequence or order of the constituent components. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Throughout the specification, unless explicitly described to the contrary, the word "comprise" and variations such as "comprises" or "comprising" will be understood to imply the inclusion of stated elements but not the exclusion of any other elements. In addition, the terms "unit", "-er", "-or", and "module" described in the specification mean units for processing at least one function and operation, and can be implemented by hardware components or software components and combinations thereof.

Although exemplary embodiment is described as using a plurality of units to perform the exemplary process, it is understood that the exemplary processes may also be performed by one or plurality of modules. Additionally, it is understood that the term controller/control unit refers to a hardware device that includes a memory and a processor and is specifically programmed to execute the processes described herein. The memory is configured to store the modules and the processor is specifically configured to execute said modules to perform one or more processes which are described further below.

Further, the control logic of the present disclosure may be embodied as non-transitory computer readable media on a computer readable medium containing executable program instructions executed by a processor, controller or the like. Examples of computer readable media include, but are not limited to, ROM, RAM, compact disc (CD)-ROMs, magnetic tapes, floppy disks, flash drives, smart cards and optical data storage devices. The computer readable medium can also be distributed in network coupled computer systems so that the computer readable media is stored and executed in a distributed fashion, e.g., by a telematics server or a Controller Area Network (CAN).

Unless specifically stated or obvious from context, as used herein, the term “about” is understood as within a range of normal tolerance in the art, for example within 2 standard deviations of the mean. “About” can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term “about”.

Hereinafter, embodiments of the present disclosure will be described in detail with reference to FIGS. 1 to 6.

FIG. 1 is a block diagram showing the configuration of a vehicle control device according to an exemplary embodiment of the present disclosure.

Referring to FIG. 1, a vehicle control device 101 may include a processor 103, an alcohol sensor 105, a communication circuit 107, and a memory 109.

The processor 103, the alcohol sensor 105, the communication circuit 107, and the memory 109 may be electronically and/or operably coupled with each other by an electronic component such as a communication bus.

According to an exemplary embodiment, hereinafter, combining pieces of hardware operatively may mean a direct connection or an indirect connection between the pieces of hardware being established in a wired or wireless manner such that first hardware of the pieces of hardware is controlled by second hardware of the pieces of hardware. The type and/or number of hardware included in the vehicle control device 101 is not limited to that illustrated in FIG. 1. For example, the vehicle control device 101 may include only some of the hardware components shown in FIG. 1.

According to an exemplary embodiment, the processor 103 of the vehicle control device 101 may acquire driver information including at least one of a driver’s age, license acquisition date, whether the driver is registered as a commercial driver, or information about the driver’s proficiency in driving, or any combination thereof, via the memory 109, or via the communication circuit 107, or through input from the driver to provide the driver information. The driver’s proficiency is likely to be lower when the driver’s driving experience, as determined from the driver’s license acquisition date, is less than a specified period of time. Conversely, proficiency is expected to be higher when the driver’s driving experience is greater than the specified period of time.

According to an exemplary embodiment, the input from the driver may be acquired via a mobile application and transferred to a host vehicle, but embodiments of the present disclosure may not be limited thereto. The processor 103 of the vehicle control device 101 may retrieve and store the driver’s information when it links with an external service or logging into a linked account within the application settings.

According to an exemplary embodiment, the processor 103 of the vehicle control device 101 may acquire a region in which the host vehicle is located, and legal limits for enforcing drunk driving corresponding to the region in which the host vehicle is located.

According to an exemplary embodiment, a BAC limit included in the legal limits for enforcing drunk driving may be determined based on the region in which the host vehicle is located, information about the driver’s proficiency in driving identified from the driver license acquisition date, and whether the driver is registered as a commercial driver. A commercial driver may include a driver who operates a revenue-generating vehicle (e.g., delivery truck, bus, taxi).

For example, the BAC limit (e.g., approximately 0.08%) above which a driver who is not registered as a commercial driver is subject to sanctions may be greater than the BAC limit (e.g., approximately 0.04%) above which a driver who is registered as a commercial driver is subject to sanctions.

For example, the BAC limit (e.g., approximately 0.00%) above which a driver under a certain age (e.g., 21 years of age) is subject to sanctions may be smaller than the BAC limit (e.g., approximately 0.08%) above which a driver over a certain age is subject to sanctions.

In an exemplary embodiment, the BAC limit above that triggers sanctions may vary according to a region in which the host vehicle is located.

For example, in Italy, the BAC limit above which a driver is subject to sanctions may be constant (e.g., approximately 0.5 g/L), regardless of whether the driver is registered as a commercial driver.

For example, in Switzerland, the BAC limit (e.g., approximately 0.5 g/L) above which a driver who is not registered as a commercial driver is subject to sanctions may be greater than the BAC limit (e.g., approximately 0.1 g/L) above which a driver who is registered as a commercial driver is subject to sanctions.

For example, in France, the BAC limit (e.g., approximately 0.5 g/L) above which a driver who is not registered as a commercial driver is subject to sanctions may be greater than the BAC limit (e.g., approximately 0.2 g/L) above which a driver who is registered as a commercial driver is subject to sanctions.

For example, in Germany, the BAC limit (e.g., approximately 0.5 g/L) above which a driver who is not registered as a commercial driver is subject to sanctions may be greater than the BAC limit (e.g., approximately 0.0 g/L) above which a driver who is registered as a commercial driver is subject to sanctions.

For example, in Spain, the BAC limit (e.g., approximately 0.5 g/L) above which a driver who is not registered as a commercial driver is subject to sanctions may be greater than the BAC limit (e.g., approximately 0.3 g/L) above which a driver who is registered as a commercial driver is subject to sanctions.

According to an exemplary embodiment, penalties due to the driver’s blood alcohol concentration may be included in the legal limits.

For example, in the New Jersey state of United States, a driver whose blood alcohol concentration exceeds about 0.08% may be subject to a three-month license suspension. For example, in the New York state of United States, a driver whose blood alcohol concentration exceeds about 0.05% may be subject to a three-month license suspension.

According to an exemplary embodiment, the higher the driver’s blood alcohol concentration, the more severe the penalties imposed on the driver.

For example, the penalty for having a blood alcohol concentration that falls within a specified first concentration range (e.g., not less than about 0.08% and less than about 0.15%) may be less than the penalty for having a blood alcohol concentration that falls within a specified second concentration range (e.g., not less than about 0.15%) that is different from the first concentration range. For example, the penalty may include a fine, license suspension, or mandatory training.

According to an exemplary embodiment, the processor 103 of the vehicle control device 101 may measure the blood alcohol concentration of a driver via the alcohol sensor 105 upon determining that the driver information corresponds to the driver, using an authentication method that includes at least one of authentication via a camera, authentication via fingerprint recognition, or authentication via mobile, or any combination thereof.

For example, if a driver not represented by the driver information is preparing to drive, the processor 103 of the vehicle control device 101 may reacquire the driver information without identifying a legal limit for enforcing drunk driving based on the driver information.

According to an exemplary embodiment, the processor 103 of the vehicle control device 101 may determine that a host vehicle is scheduled to operate upon determining at least one of the closure of the door of a driver seat where the driver is located in the host vehicle, or the buckling of the seat belt of the driver seat, or any combination thereof. The processor 103 of the vehicle control device 101 may measure the blood alcohol concentration of the driver via the alcohol sensor 105 upon determining that the host vehicle is scheduled to be operated.

According to an exemplary embodiment, the processor 103 of the vehicle control device 101 may measure the blood alcohol concentration of a driver operating the host vehicle via the alcohol sensor 105.

For example, the alcohol sensor 105 may measure the blood alcohol concentration of the driver based on measuring alcohol in the driver's exhaled breath. In one example, the alcohol sensor 105 may measure the driver's blood alcohol concentration in response to the driver's behavior of directing exhaled breath to the alcohol sensor 105. In one example, the alcohol sensor 105 may measure the driver's blood alcohol concentration based on alcohol contained in the air inside the vehicle.

For example, the alcohol sensor 105 may measure the driver's blood alcohol concentration in response to the driver's behavior of indicating a request to measure the blood alcohol concentration. For example, the alcohol sensor 105 may measure the driver's blood alcohol concentration independent of the driver's behavior of indicating a request to measure the blood alcohol concentration.

According to an exemplary embodiment, the processor 103 of the vehicle control device 101 may identify whether the measured blood alcohol concentration falls within a BAC range (e.g., greater than or equal to about 0.08%) for which a driver is subject to sanctions, which is identified based on the driver information and the legal limits.

For example, the processor 103 of the vehicle control device 101 may identify whether the blood alcohol concentration falls within the legal range by comparing the blood alcohol concentration of the driver to a BAC limit corresponding to the driver information, among at least one BAC limits included in the legal limits.

According to an exemplary embodiment, the processor 103 of the vehicle control device 101 may load, from the memory 109, the at least one BAC limit for enforcing drunk driving corresponding to a specific range that includes a region in which the host vehicle is located or acquire the at least one BAC limit via the communication circuit 107. According to an exemplary embodiment, the specific range may include a physical or conceptual range. For example, the specific range may represent a physical range within a specified distance from a region in which the host vehicle is located. In another example, the specific range may represent a conceptual range that represents a state, or a country, that includes the region in which the host vehicle is located.

According to an exemplary embodiment, the processor 103 of the vehicle control device 101 may perform control such that the host vehicle is in a stop state if the blood alcohol concentration falls within a BAC range in which a driver is subject to sanctions, according to the legal limits. For example, if the blood alcohol concentration falls within the BAC range in which a driver is subject to sanctions according to the legal limits, the processor 103 of the vehicle control device 101 may control the host vehicle to turn off an ignition or to be disabled, if the blood alcohol concentration falls within the BAC range in which a driver is subject to sanctions according to the legal limits. For example, the processor 103 of the vehicle control device 101 may control the host vehicle such that the speed of the host vehicle gradually decreases over time if the blood alcohol concentration falls within the BAC range in which a driver is subject to sanctions according to the legal limits.

According to an exemplary embodiment, the processor 103 of the vehicle control device 101 may control the host vehicle according to a driver's operation if the blood alcohol concentration is in a BAC range in which a driver is not subject to sanctions according to the legal limits. For example, the processor 103 of the vehicle control device 101 may control the host vehicle by an autonomous driving device or a driving assistance device in response to a driver's operation (e.g., an input to activate an autonomous driving mode). For example, the processor 103 of the vehicle control device 101 may perform control to operate the host vehicle in response to a driver's operation (e.g., steering wheel operation, braking system operation).

According to an exemplary embodiment, the processor 103 of the vehicle control device 101 may reacquire driver information and re-measure the driver's blood alcohol concentration via the alcohol sensor, based on the occurrence of a driver change event that includes at least one of opening of a driver seat door, unbuckling of a driver seat belt, or stopping driving after driving, or any combination thereof. This is because there is a high possibility that the driver will be changed if at least one of opening of a driver seat door, unbuckling of a driver seat belt, or stopping driving after driving, or any combination thereof occurs.

According to an exemplary embodiment, based on the occurrence of the driver change event, the processor 103 of the vehicle control device 101 may request the driver to re-measure the blood alcohol concentration if driving has stopped, or request the driver to re-measure the blood alcohol concentration after a recommendation to stop.

According to an exemplary embodiment, at the boundary of regions with different BAC limits for enforcing drunk driving, the processor 103 of the vehicle control device 101 may not acquire driver information based on a driver change event occurring if global positioning system (GPS) information indicative of the location of the host vehicle is not received, and then, if the GPS information indicative of the location of the host vehicle is received, reacquire the driver information based on the driver change event identified while the GPS information was not received.

According to an exemplary embodiment, instances where global positioning system (GPS) information indicative of the location of the host vehicle is not received may include instances where the host vehicle is located in an environment where the GPS information is difficult to receive, such as a tunnel or underground parking lot.

According to an exemplary embodiment, if global positioning system (GPS) information indicating the location of the host vehicle is not received, the processor of the vehicle control device may determine whether the driver's blood alcohol concentration is greater than a BAC limit according to the most stringent of the BAC limits contained in the legal limits of nearby regions.

In other words, the processor of the vehicle control device may determine whether the driver's blood alcohol concentration is greater than a BAC limit according to the lowest of the BAC limits contained in the legal limits of the nearby regions if GPS information indicating the location of the host vehicle is not received.

According to an exemplary embodiment, the processor 103 of the vehicle control device 101 may re-measure the driver's blood alcohol concentration via the alcohol sensor 105 based on a change in at least one of at least one BAC limit for enforcing drunk driving, or a region in which the host vehicle is located, or any combination thereof. For example, the processor 103 of the vehicle control device 101 may re-measure the driver's blood alcohol concentration if the region in which the host vehicle is located changes, even though the BAC limit does not change.

According to an exemplary embodiment, if a region in which the host vehicle is located has changed, the processor 103 of the vehicle control device 101 may re-measure the driver's blood alcohol concentration via the alcohol sensor 105. This re-measurement is based on the BAC limit from the new region's legal standards for drunk driving, especially if this limit is stricter than the limit from the previous region.

According to an exemplary embodiment, the processor 103 of the vehicle control device 101 may measure the driver's blood alcohol concentration via the alcohol sensor and provide a warning to the driver about drunk driving before turning on an ignition or may re-measure the driver's blood alcohol concentration via the alcohol sensor after turning on the ignition.

Figure 2:
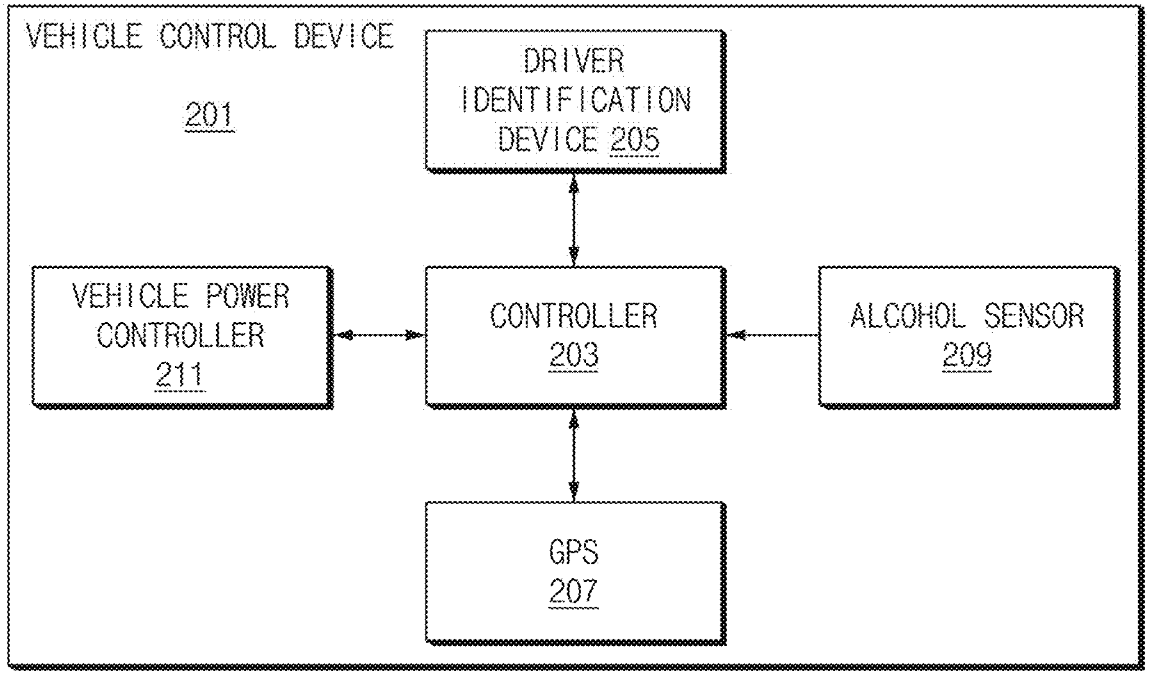
FIG. 2 is a block diagram illustrating another configuration of a vehicle control device according to an exemplary embodiment of the present disclosure.

FIG. 2 is a block diagram illustrating another configuration of a vehicle control device according to an exemplary embodiment of the present disclosure.

Referring to FIG. 2, a vehicle control device 201 may include a controller 203, a driver identification device 205, a global positioning system (GPS) 207, an alcohol sensor 209, and a vehicle power controller 211.

According to an exemplary embodiment, the controller 203 may perform vehicle control based on a measured blood alcohol concentration. The controller 203 may acquire regional information about a location in which a host vehicle is located from the GPS 207. The controller 203 may acquire a measured value of the blood alcohol concentration from the alcohol sensor 209. The controller 203 may determine whether the measured blood alcohol concentration falls within a legal BAC limit range in which a driver is subject to sanctions according to the legal limits. If the measured blood alcohol concentration falls within the legal BAC range, the controller 203 may transmit a signal for turning off an ignition to the vehicle power controller 211.

According to an exemplary embodiment, the driver identification device 205 may identify driver information corresponding to a driver. For example, the driver information may be identified as corresponding to the driver by an authentication method including at least one of authentication via a camera in the host vehicle (e.g., an in-cabin camera), authentication via a mat sensor, authentication via fingerprint recognition, or authentication via a mobile device, or any combination thereof. The mat sensor may refer to a sensor that identifies a pressure applied to a seat. The driver identification device 205 may identify the driver based on the magnitude of the pressure applied to the seat.

According to an exemplary embodiment, the GPS 207 may identify a region in which the host vehicle is located.

According to an exemplary embodiment, the alcohol sensor 209 may be in a mode for measuring a blood alcohol concentration in response to the driver's motion, or may be in a mode for measuring a blood alcohol concentration independent of the driver's motion. According to an exemplary embodiment, the alcohol sensor 209 may transmit the measured blood alcohol concentration to the controller 203.

According to an exemplary embodiment, the vehicle power controller 211 may control the vehicle to turn on or turn off an ignition. For example, the vehicle power controller 211 may receive a signal for turning on an ignition, or a signal for turning off the ignition, from the controller 203.

Figure 3:
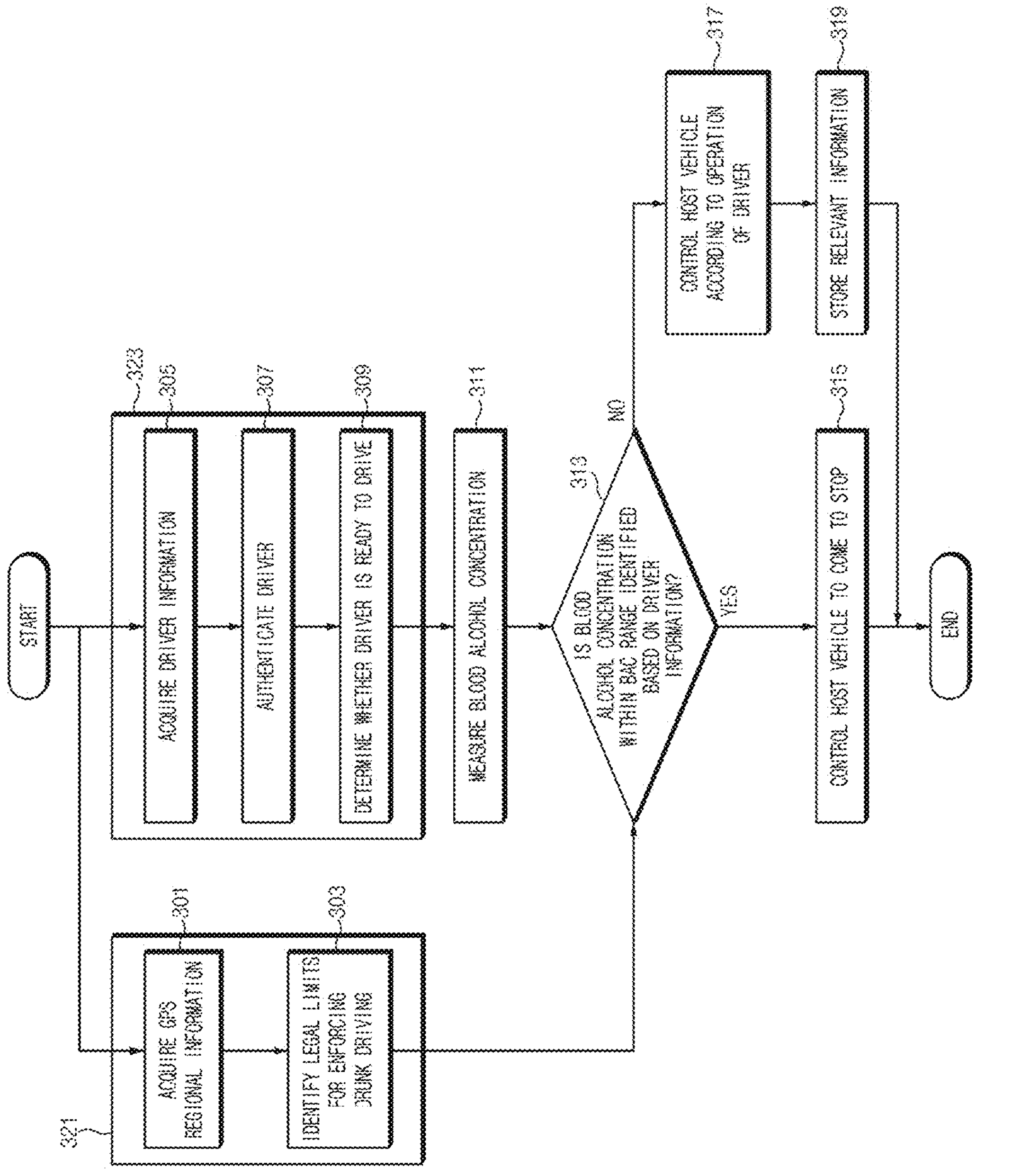
FIG. 3 illustrates a flowchart of operation of a vehicle control device for identifying whether a blood alcohol concentration falls within a legal BAC range identified based on driver information in a vehicle control device or a vehicle control method, according to an exemplary embodiment of the present disclosure.

FIG. 3 illustrates a flowchart of operation of a vehicle control device for identifying whether a blood alcohol concentration falls within a legal BAC range identified based on driver information in a vehicle control device, or a vehicle control method, according to an exemplary embodiment of the present disclosure.

Hereinafter, it is assumed that the processor 103 of the vehicle control device 101 of FIG. 1 performs the process of FIG. 3. Also, in the description of FIG. 3, the operations described as being performed by the processor of the vehicle control device may be understood as being controlled by the processor 103 of the vehicle control device 101.

Referring to FIG. 3, in a first operation 301, the processor of the vehicle control device may acquire GPS regional information. The GPS regional information may indicate a region in which the host vehicle is located.

In a second operation 303, the processor of the vehicle control device may identify legal limits for enforcing drunk driving. The legal limits for enforcing drunk driving may correspond to the region in which the host vehicle is located.

The first operation 301 and the second operation 303 may be included in an operation 321 for acquiring regional information and legal limits for enforcing drunk driving based on the regional information.

In a third operation 305, the processor of the vehicle control device may acquire driver information. The driver information may include at least one of age of the driver, date of license acquisition, whether the driver is registered as a commercial driver, or information about the driver's proficiency in driving, or any combination thereof.

In a fourth operation 307, the processor of the vehicle control device may authenticate the driver. To prevent drunk driving enforcement based on driver information that does not correspond to the driver, the processor of the vehicle control device may identify that the driver matches the actual driver using an authentication method that includes at least one of: authentication via camera, authentication via fingerprint recognition, or authentication via mobile, or authentication via matte sensor, or any combination thereof.

In a fifth operation 309, the processor of the vehicle control device may determine whether the driver is ready to drive. The processor of the vehicle control device may determine that the driver is ready to drive upon determining at least one of a closure of the door of a driver seat where the driver is located in the host vehicle, a fastening of a seat belt of the driver seat, or an identification of pressure from a mat sensor, or any combination thereof.

The third operation 305, the fourth operation 307, and the fifth operation 309 may be included in an operation 323 for determining whether the driver matches a person represented by the driver information. If the driver matches the person represented by the driver information and is preparing to drive, the processor of the vehicle control device may assess whether the driver is drunk based on the driver information.

In a sixth operation 311, the processor of the vehicle control device may measure a blood alcohol concentration.

In a seventh operation 313, the processor of the vehicle control device may identify whether the blood alcohol concentration falls within a BAC range in which the driver is subject to sanctions according to legal limits, which is identified based on the driver information. If the blood alcohol concentration falls within the BAC range in which the driver is subject to sanctions according to the legal limits, which is identified based on the driver information, the processor of the vehicle control device may perform an eighth operation 315. If the blood alcohol concentration is outside the BAC range in which the driver is subject to sanctions according to the legal limits, which is identified based on the driver information, the processor of the vehicle control device may perform a ninth operation 317. The legal limit may be identified based on a BAC limit corresponding to the driver information among BAC limits included in BAC limits for enforcing drunk driving.

In the eighth operation 315, the processor of the vehicle control device may control the host vehicle to come to a stop. For example, to reduce the likelihood of an accident caused by drunk driving, the processor of the vehicle control device may control the host vehicle to turn off the ignition, to be disabled, or to cause the speed of the host vehicle to gradually decrease over time.

In a ninth operation 317, the processor of the vehicle control device may control the host vehicle in response to an operation of the driver. For example, the processor of the vehicle control device may control the host vehicle to be driven by an autonomous driving device or a driver assistance device in response to a driver's operation (e.g., an input to activate an autonomous driving mode), or may control the host vehicle to be operated in response to a driver's operation (e.g., steering wheel operation, braking system operation).

In a tenth operation 319, the processor of the vehicle control device may store relevant information. The relevant information may include driver information, a result of determining whether the blood alcohol concentration falls within a BAC range in which the driver is subject to sanctions according to legal limits, a region where the host vehicle is located, a time of day, and a result value, such as whether the vehicle is able to be controlled based on the driver's operation. The relevant information may be transferred to other entities involved in the operation of the vehicle or used to improve accuracy, as needed.

Figure 4:
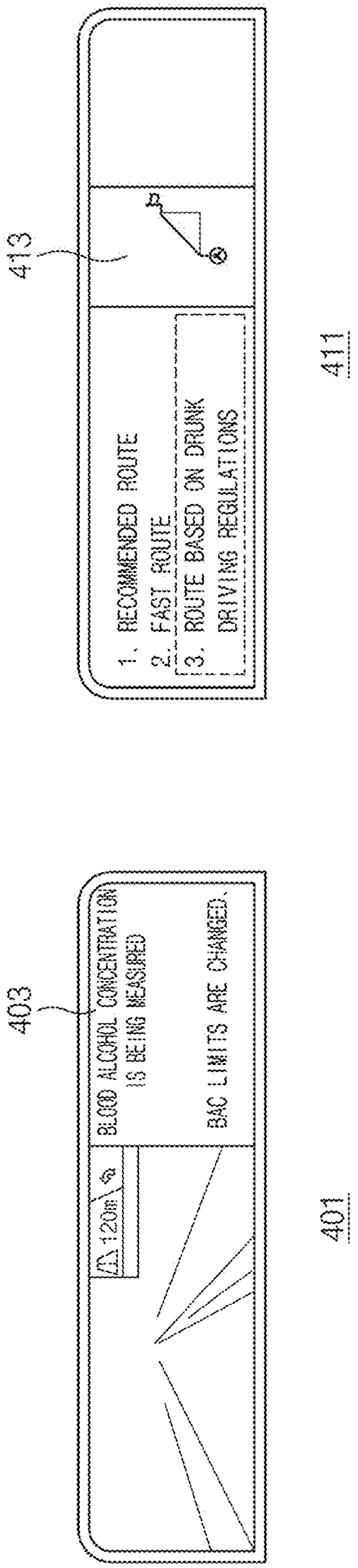
FIG. 4 illustrates an example of providing a notification or route to a driver in a vehicle control device or a vehicle control method, according to an exemplary embodiment of the present disclosure.

FIG. 4 illustrates an example of providing a notification or a route to a driver in a vehicle control device or a vehicle control method, according to an exemplary embodiment of the present disclosure.

Referring to FIG. 4, a first situation 401 may represent a situation in which there is a need to measure a blood alcohol concentration or a change in BAC limit for enforcing drunk driving. A first screen 403 may represent a notification provided to a driver in the first situation 401.

A second situation 411 may represent a situation of navigating a route from an origin to a destination. A second screen 413 may represent a notification of requesting input from the driver to select whether to navigate the route based on BAC limits for enforcing drunk driving.

According to an exemplary embodiment, in the first screen 403, the processor of the vehicle control device may provide the driver with a notification related to measuring a blood alcohol concentration based on when a blood alcohol concentration should be measured, or when a BAC limit that is included in the legal limits for enforcing drunk driving changes.

According to an exemplary embodiment, the information related to the alcohol concentration measurement may be managed in a cluster, and a notification related to the alcohol concentration measurement may be provided to the driver if a new event occurs. The notification related to the alcohol concentration measurement may be provided to the driver in the form of a head up display (HUD). The notification related to the alcohol concentration measurement may be provided to the driver via voice.

According to an exemplary embodiment, the processor of the vehicle control device may provide the driver with a notification to measure the alcohol concentration in two methods.

According to a first method, the processor of the vehicle control device may provide the driver with a notification, such as the first screen 403, based on a change in the region in which the host vehicle is located or a driver change event occurring.

According to a second method, if a region in which the host vehicle is located has changed, the processor 103 of the vehicle control device 101 may provide the driver with a notification, such as the first screen 403 based on a BAC limit included in the legal limits for enforcing drunk driving, which corresponds to the region after the change in region being smaller than a BAC limit included in the legal limits for enforcing drunk driving, which corresponds to the region before the change in region.

According to a second method, the processor of the vehicle control device may not provide the driver with a notification such as the first screen 403 if the region in which the host vehicle is located changes and the BAC limit corresponding to the region after the change is equal to or greater than the BAC limit corresponding to the region before the change.

According to an exemplary embodiment, in the second screen 413, the processor of the vehicle control device may provide the driver with a notification of requesting input from the driver to select whether to navigate a route based on the legal limits for enforcing drunk driving.

According to an exemplary embodiment, if the driver inputs the origin and destination for a route, the vehicle's control device processor can provide a route where the blood alcohol concentration (BAC) limit, based on legal limits for drunk driving enforcement, is not lower than the BAC limit at the route's origin for each region included in the route. This is determined from the driver's input.

According to another embodiment, if input from the driver to navigate a route from an origin to a destination based on the legal limits for enforcing drunk driving is acquired, the processor of the vehicle control device may provide the driver with a route in which the BAC limit included in the legal limits for enforcing drunk driving corresponding to each of at least one region included in the route to the destination is kept constant, based on the input from the driver.

Figure 5:
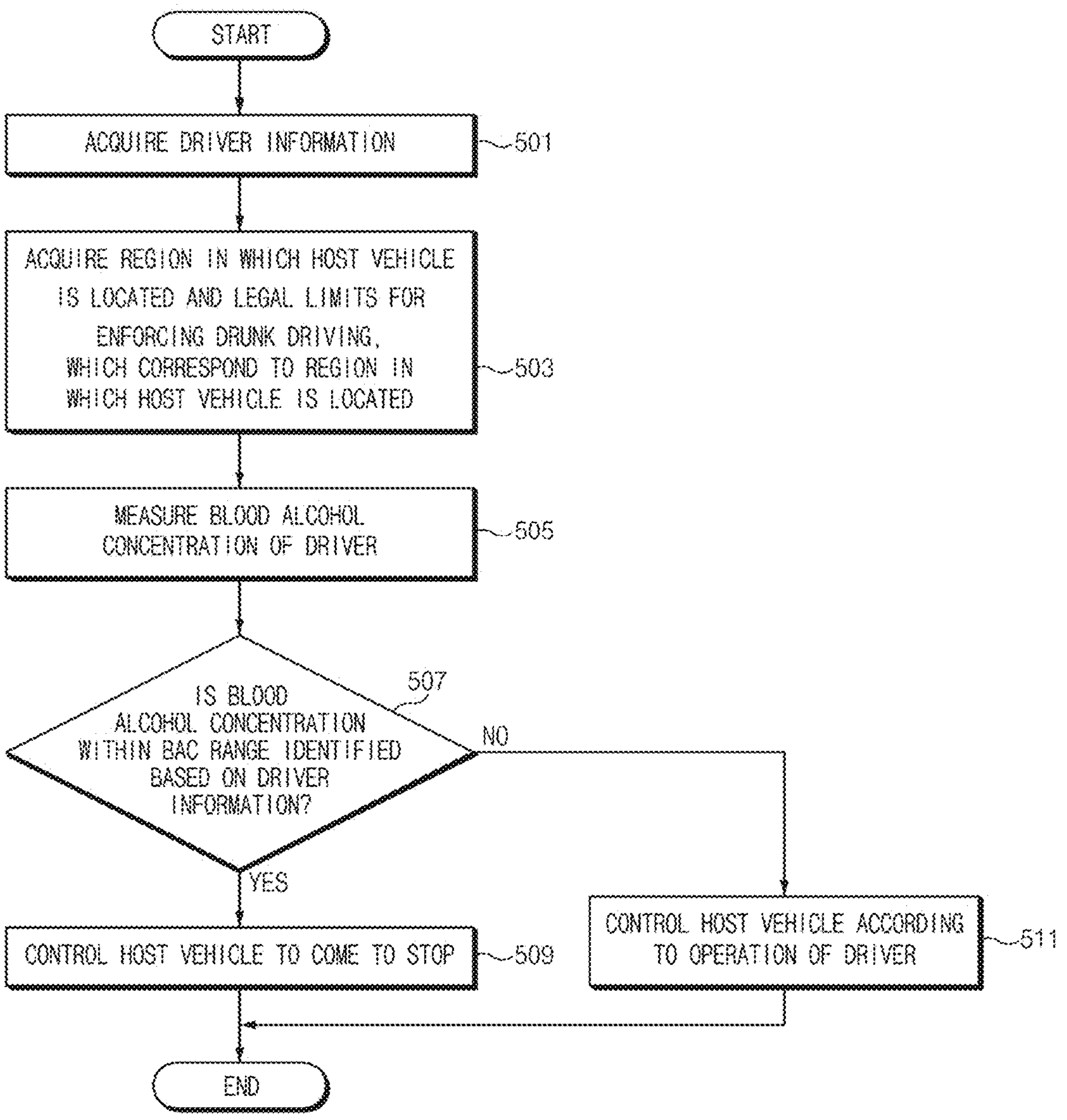
FIG. 5 illustrates a flow of operations of a vehicle control device for controlling a host vehicle in a vehicle control device or a vehicle control method, according to an exemplary embodiment of the present disclosure.

FIG. 5 illustrates a flow of operations of a vehicle control device for controlling a host vehicle in a vehicle control device or a vehicle control method, according to an exemplary embodiment of the present disclosure.

Hereinafter, it is assumed that the processor 103 of the vehicle control device 101 of FIG. 1 performs the process of FIG. 5. Also, in the description of FIG. 5, the operations described as being performed by the processor of the vehicle control device may be understood as being controlled by the processor 103 of the vehicle control device 101.

Referring to FIG. 5, in a first operation 501, the processor of the vehicle control device may acquire driver information. The driver information may include at least one of age of the driver, date of license acquisition, whether the driver is registered as a commercial driver, or information about the driver's proficiency in driving, or any combination thereof.

In a second operation 503, the processor of the vehicle control device may acquire a region in which the host vehicle is located, and BAC limits for enforcing drunk driving corresponding to the region.

In a third operation 505, the processor of the vehicle control device may measure the blood alcohol concentration of a driver. The blood alcohol concentration of the driver may be measured by an alcohol sensor.

In a fourth operation 507, the processor of the vehicle control device may identify whether the blood alcohol concentration falls within a BAC range by a legal limit identified based on the driver information. If the blood alcohol concentration falls within the BAC range by the legal limit identified based on the driver information, the processor of the vehicle control device may perform a fifth operation 509. If the blood alcohol concentration is outside the BAC range by the legal limit identified based on the driver information, the processor of the vehicle control device may perform a sixth operation 511. The legal limit may be identified based on BAC limits for enforcing drunk driving based on the region in which the host vehicle is located, and the driver information.

In the fifth operation 509, the processor of the vehicle control device may control the host vehicle to come to stop.

In the sixth operation 511, the processor of the vehicle control device may control the host vehicle in response to an operation of the driver.

Figure 6:
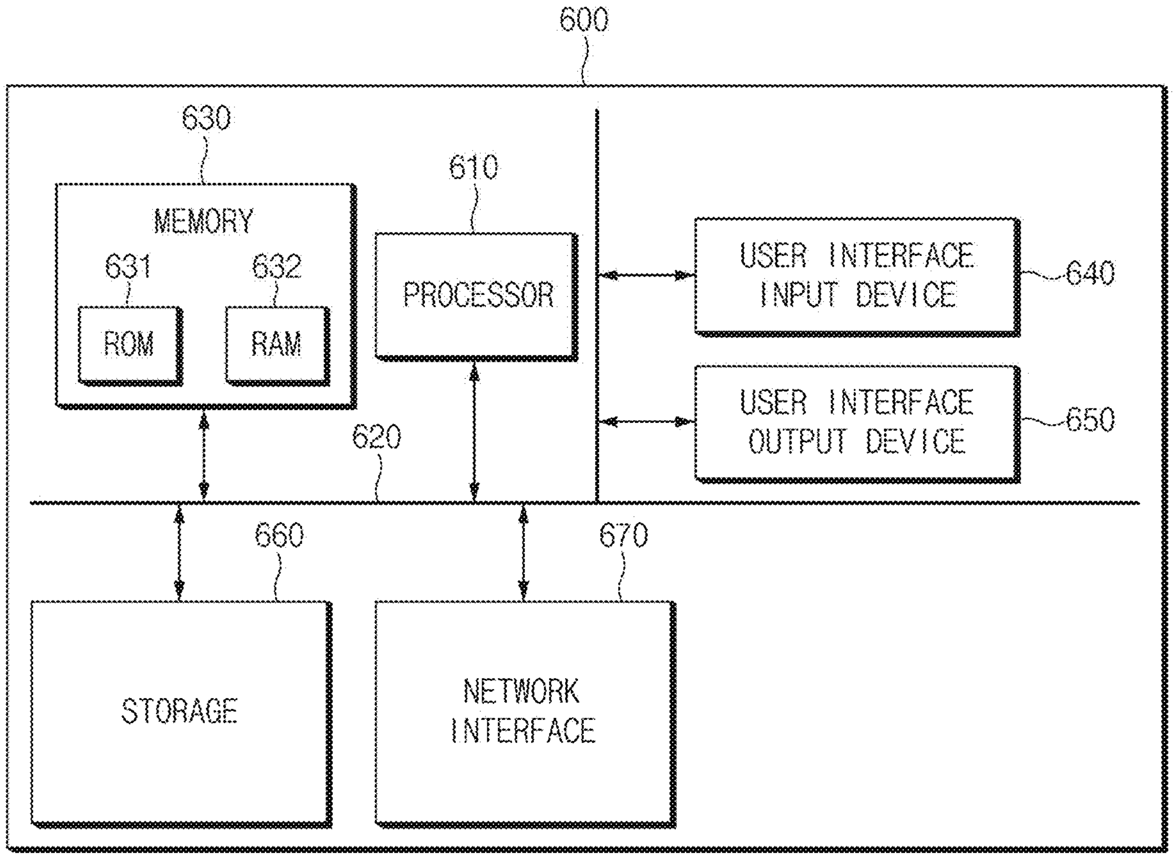
FIG. 6 illustrates a computing system related to a vehicle control device or a vehicle control method according to an exemplary embodiment of the present disclosure.

FIG. 6 illustrates a computing system related to a vehicle control device or a vehicle control method according to an exemplary embodiment of the present disclosure.

Referring to FIG. 6, a computing system 600 may include at least one processor 610, a memory 630, a user interface input device 640, a user interface output device 650, storage 660, and a network interface 670, which are connected with each other via a bus 620.

The processor 610 may be a central processing unit (CPU) or a semiconductor device that processes instructions stored in the memory 630 and/or the storage 660. The memory 630 and the storage 660 may include various types of volatile or non-volatile storage media. For example, the memory 630 may include a ROM (Read Only Memory) 631 and a RAM (Random Access Memory) 632.

Thus, the operations of the method or the algorithm described in connection with the embodiments disclosed herein may be embodied directly in hardware or a software module executed by the processor 610, or in a combination thereof. The software module may be stored on a storage medium (that is, the memory 630 and/or the storage 660) such as a RAM, a flash memory, a ROM, an EPROM, an EEPROM, a register, a hard disk, a removable disk, and a CD-ROM.

The exemplary storage medium may be coupled to the processor 610, and the processor 610 may read information out of the storage medium and may record information in the storage medium. Alternatively, the storage medium may be integrated with the processor 610. The processor and the storage medium may be housed in an application specific integrated circuit (ASIC). The ASIC may be housed within a user terminal. In another case, the processor and the storage medium may be housed in the user terminal as separate components.

The above description is merely illustrative of the technical idea of the present disclosure, and various modifications and variations may be made without departing from the essential characteristics of the present disclosure by those skilled in the art to which the present disclosure pertains.

Accordingly, the embodiment disclosed in the present disclosure is not intended to limit the technical idea of the present disclosure but to describe the present disclosure, and the scope of the technical idea of the present disclosure is not limited by the embodiment. The scope of protection of the present disclosure should be interpreted by the following claims, and all technical ideas within the scope equivalent thereto should be construed as being included in the scope of the present disclosure.

The present technology may acquire drunk driving information that changes depending on a region where a host vehicle is located.

Further, the present technology may identify legal limits for enforcing drunk driving, which vary depending on a driver.

Further, the present technology may reduce the incidence of accidents caused by drunk driving.

Further, the present technology may improve the accuracy of determination of whether there is drunk driving.

In addition, various effects may be provided that are directly or indirectly understood through the disclosure.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims.

What is claimed is:

1. A vehicle control device comprising:

a memory configured to store program instructions;

an alcohol sensor configured to measure a blood alcohol concentration (BAC) of a driver operating a host vehicle; and a processor configured to execute the program instructions, wherein the processor is configured to:

acquire driver information, comprising at least one of an age of the driver, license acquisition date, whether the driver is registered as a commercial driver and information about the driver's driving proficiency;

acquire a region in which the host vehicle is located, and legal limits for enforcing drunk driving corresponding to the region;

measure the BAC of the driver via the alcohol sensor;

identify whether the measured BAC falls within a BAC range in which the driver is subject to sanctions according to the legal limits, the BAC range being determined based on the driver information and the legal limits;

control the host vehicle to come to a stop if the BAC falls within the BAC range; and provide the driver with a route in which the BAC limit included in legal limits for enforcing drunk driving corresponding to each of at least one region included in a route to a destination is kept not smaller than the BAC limit included in legal limits for enforcing drunk driving corresponding to an origin of the route, based on an input for acquiring the route from the driver.

2. The vehicle control device of claim 1, wherein the processor is configured to measure the BAC of the driver via the alcohol sensor upon determining at least one of closure of a door of a driver seat where the driver is located in the host vehicle, or fastening of a seat belt of the driver seat, or any combination thereof.

3. The vehicle control device of claim 2, wherein the processor is configured to:

reacquire the driver information based on occurrence of a driver change event comprising at least one of opening of the door of the driver seat, unbuckling of the seat belt of the driver seat, or stopping driving after driving, or any combination thereof; and re-measure the BAC of the driver via the alcohol sensor.

4. The vehicle control device of claim 1, wherein the processor is configured to:

acquire at least one BAC limit included in legal limits for enforcing drunk driving corresponding to a specific area comprising the region in which the host vehicle is located; and re-measure the BAC of the driver via the alcohol sensor based on a change in at least one of the at least one BAC limit for enforcing drunk driving, or the region in which the host vehicle is located, or any combination thereof.

5. The vehicle control device of claim 1, wherein the processor is configured to re-measure the BAC of the driver via the alcohol sensor based on, after or before the region in which the host vehicle is located has been changed, a BAC limit included in legal limits for enforcing drunk driving, which corresponds to the region after the change in region being smaller than a BAC limit included in legal limits for enforcing drunk driving, which corresponds to the region before the change in region.

6. The vehicle control device of claim 1, further comprising:

a camera, wherein the processor is configured to:

measure the BAC of the driver via the alcohol sensor upon determining that the driver information corresponds to the driver in an authentication method that comprises at least one of authentication via the camera, authentication via fingerprint recognition, and authentication via mobile.

7. The vehicle control device of claim 3, wherein the processor is configured to:

control the host vehicle according to the operation of the driver without acquiring the driver information based on occurrence of the driver change event if global positioning system (GPS) information indicating a location of the host vehicle is not received at a boundary of regions with different BAC limits of legal limits for enforcing drunk driving; and reacquire the driver information based on the driver change event identified while the GPS information is not received if the GPS information indicating the location of the host vehicle is received.

8. The vehicle control device of claim 1, wherein the processor is configured to:

acquire the driver information based on the driver's input for providing the driver information if the host vehicle comprises a public vehicle which multiple drivers are able to use, or a commercial vehicle that generates profit through driving; or acquire the driver information via the memory or acquire the driver information via a communication circuit if the host vehicle comprises a vehicle other than the public vehicle and the commercial vehicle.

9. The vehicle control device of claim 1, wherein the processor is configured to provide the driver with a notification for guiding the driver to measure the BAC based on a time at which the BAC needs to be measured, or a time at which a BAC limit included in the legal limits changes.

10. The vehicle control device of claim 1, wherein the processor is configured to:

measure the BAC via the alcohol sensor in response to the driver's operation for measuring the BAC; or measure the BAC via the alcohol sensor regardless of the driver's operation.

11. The vehicle control device of claim 1, wherein the processor is configured to:

measure the BAC of the driver via the alcohol sensor before turning on an ignition of the host vehicle; and provide the driver with a warning about drunk driving, or re-measure the blood alcohol concentration of the driver via the alcohol sensor after turning on the ignition.

12. A vehicle control method comprising:

acquiring driver information, comprising at least one of an age of a driver, license acquisition date, whether the driver is registered as a commercial driver, and information about the driver's driving proficiency;

acquiring a region in which a host vehicle is located, and legal limits for enforcing drunk driving corresponding to the region;

measuring the blood alcohol concentration (BAC) of the driver via an alcohol sensor;

identifying whether the measured BAC falls within a BAC range in which the driver is subject to sanctions according to the legal limits, the BAC range being determined based on the driver information and the legal limits;

controlling the host vehicle to come to a stop if the BAC falls within the BAC range; and providing the driver with a route in which the BAC limit included in legal limits for enforcing drunk driving corresponding to each of at least one region included in a route to a destination is kept not smaller than the BAC limit included in legal limits for enforcing drunk driving corresponding to an origin of the route, based on an input for acquiring the route from the driver.

13. The vehicle control method of claim 12, wherein the measuring of the BAC of the driver via the alcohol sensor comprises measuring BAC of the driver via the alcohol sensor upon determining at least one of closure of a door of a driver seat where the driver is located in the host vehicle, and fastening of a seat belt of the driver seat.

14. The vehicle control method of claim 13, further comprising:

reacquiring the driver information based on occurrence of a driver change event comprising at least one of opening of the door of the driver seat, unbuckling of the seat belt of the driver seat, and stopping driving after driving; and re-measuring the BAC of the driver via the alcohol sensor.

15. The vehicle control method of claim 12, further comprising:

acquiring at least one BAC limit included in legal limits for enforcing drunk driving corresponding to a specific area comprising the region in which the host vehicle is located; and re-measuring the BAC of the driver via the alcohol sensor based on a change in at least one of the at least one BAC limit for enforcing drunk driving, and the region in which the host vehicle is located.

16. The vehicle control method of claim 12, further comprising:

re-measuring the BAC of the driver via the alcohol sensor based on, after or before the region in which the host vehicle is located has been changed, a BAC limit included in legal limits for enforcing drunk driving, which corresponds to the region after the change in region being smaller than a BAC limit included in legal limits for enforcing drunk driving, which corresponds to the region before the change in region.

17. The vehicle control method of claim 12, wherein the measuring of the BAC of the driver via the alcohol sensor comprises measuring the BAC of the driver via the alcohol sensor upon determining that the driver information corresponds to the driver in an authentication method that comprises at least one of authentication via the camera, authentication via fingerprint recognition, and authentication via mobile.

18. The vehicle control method of claim 14, further comprising:

controlling the host vehicle according to the operation of the driver without acquiring the driver information based on occurrence of the driver change event if global positioning system (GPS) information indicating a location of the host vehicle is not received at a boundary of regions with different BAC limits of legal limits for enforcing drunk driving; and reacquiring the driver information based on the driver change event identified while the GPS information is not received if the GPS information indicating the location of the host vehicle is received.

19. The vehicle control method of claim 12, wherein the acquiring of the driver information, comprising at least one of the age of the driver, the license acquisition date, whether the driver is registered as the commercial driver, and information about the driver's proficiency in driving comprises:

acquiring the driver information based on the driver's input for providing the driver information if the host vehicle comprises a public vehicle which multiple drivers are able to use, or a commercial vehicle that generates profit through driving; or acquiring the driver information via a memory or acquiring the driver information via a communication circuit if the host vehicle comprises a vehicle other than the public vehicle and the commercial vehicle.

* * * * *